US010052101B2

(12) United States Patent
Kortenbach et al.

(10) Patent No.: US 10,052,101 B2
(45) Date of Patent: Aug. 21, 2018

(54) TISSUE FASTENING DEVICES AND PROCESSES THAT PROMOTE TISSUE ADHESION

(71) Applicant: Boston Scientific Scimed, Inc., Maple Grove, MN (US)

(72) Inventors: Juergen A. Kortenbach, Miami Springs, FL (US); Michael Sean McBrayer, Miami, FL (US); Alan Weisenborn, Miami, FL (US); Robert B. DeVries, Northborough, MA (US); William H. Stahley, Andover, MA (US); Jeff Wendlandt, Cambridge, MA (US); Mark L. Adams, Sandy, UT (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 689 days.

(21) Appl. No.: 14/338,589

(22) Filed: Jul. 23, 2014

(65) Prior Publication Data

US 2014/0336673 A1 Nov. 13, 2014

Related U.S. Application Data

(63) Continuation of application No. 13/549,392, filed on Jul. 13, 2012, now abandoned, which is a
(Continued)

(51) Int. Cl.
*A61B 17/068* (2006.01)
*A61B 17/064* (2006.01)
(Continued)

(52) U.S. Cl.
CPC ........ *A61B 17/068* (2013.01); *A61B 17/0643* (2013.01); *A61B 17/0644* (2013.01);
(Continued)

(58) Field of Classification Search
CPC ... A61F 2002/30467; A61F 2220/0083; A61B 17/068; A61B 17/0643; A61B 17/0644;
(Continued)

(56) References Cited

U.S. PATENT DOCUMENTS

| 1,918,889 A | 7/1933 | Bacon |
| 3,388,492 A | 6/1968 | Harley, Jr. |

(Continued)

FOREIGN PATENT DOCUMENTS

| WO | WO 01/85034 A1 | 11/2001 |
| WO | WO 02/26139 | 4/2002 |
| WO | WO 02/28289 A1 | 4/2002 |

OTHER PUBLICATIONS

PCT Invitation to Pay Additional Fees and a Communication Relating to the Results of the Partial International Search for International Application No. PCT/US03/10680, dated Nov. 28, 2003.

*Primary Examiner* — Diane Yabut
(74) *Attorney, Agent, or Firm* — Bookoff McAndrews, PLLC

(57) ABSTRACT

The invention in certain aspects relates to a surgical fastener for fastening tissue segments having tissue surfaces. The fastener includes a first fastener member having a base and a piercing element connected to the base for piercing the tissue segments to be fastened, a second fastener member having an opening for receiving and retaining the piercing element of the first fastener member such that the tissue segments to be fastened are retained between the first and second fastening members, and means for promoting adhe-
(Continued)

sion between the tissue surfaces. The invention also relates to related methods and devices for promoting adhesion of tissue segments and preventing fastener migration, especially in an endoscopic procedure for the treatment of GERD.

17 Claims, 21 Drawing Sheets

Related U.S. Application Data continuation of application No. 10/345,150, filed on Jan. 16, 2003, now Pat. No. 8,241,308, which is a continuation of application No. 10/128,508, filed on Apr. 24, 2002, now abandoned.

(51) Int. Cl.
 *A61B 17/00* (2006.01)
 *A61F 2/30* (2006.01)
(52) U.S. Cl.
 CPC .......... *A61B 17/00491* (2013.01); *A61B 2017/00004* (2013.01); *A61B 2017/00827* (2013.01); *A61B 2017/00867* (2013.01); *A61B 2017/0641* (2013.01); *A61B 2017/0647* (2013.01); *A61F 2002/30467* (2013.01); *A61F 2220/0083* (2013.01)
(58) Field of Classification Search
 CPC .... A61B 17/00491; A61B 2017/00004; A61B 2017/00827; A61B 2017/00867; A61B 2017/0641; A61B 2017/0647
 See application file for complete search history.

(56) References Cited

U.S. PATENT DOCUMENTS

| | | | |
|---|---|---|---|
| 3,623,192 A | 11/1971 | Papazian | |
| 3,825,010 A | 7/1974 | McDonald | |
| 3,831,584 A | 8/1974 | Bucalo | |
| 4,454,875 A | 6/1984 | Pratt et al. | |
| 4,471,546 A | 9/1984 | Bolling, Jr. | |
| 4,532,926 A | 8/1985 | O'Holla | |
| 4,548,202 A | 10/1985 | Duncan | |
| 4,570,623 A | 2/1986 | Ellison et al. | |
| 4,592,346 A | 6/1986 | Jurgutis | |
| 4,754,758 A | 7/1988 | Li | |
| 4,793,335 A | 12/1988 | Frey et al. | |
| 4,935,028 A | 6/1990 | Drews | |
| 4,976,715 A | 12/1990 | Bays et al. | |
| 5,013,316 A | 5/1991 | Goble et al. | |
| 5,016,369 A | 5/1991 | Parry | |
| 5,053,047 A | 10/1991 | Yoon | |
| 5,189,986 A | 3/1993 | Burkoth | |
| 5,226,908 A | 7/1993 | Yoon | |
| 5,282,829 A | 2/1994 | Hermes | |
| 5,383,897 A | 1/1995 | Wholey | |
| 5,403,312 A | 4/1995 | Yates et al. | |
| 5,403,326 A | 4/1995 | Harrison et al. | |
| 5,423,858 A | 6/1995 | Bolanos et al. | |
| 5,454,814 A | 10/1995 | Comte | |
| 5,486,195 A | 1/1996 | Myers et al. | |
| 5,549,122 A | 8/1996 | Detweilwer | |
| 5,562,694 A | 10/1996 | Sauer et al. | |
| 5,569,272 A | 10/1996 | Reed et al. | |
| 5,571,216 A | 11/1996 | Anderson | |
| 5,582,616 A | 12/1996 | Bolduc et al. | |
| 5,591,206 A | 1/1997 | Moufarrege | |
| 5,630,831 A | 5/1997 | Lahr | |
| 5,634,936 A | 6/1997 | Linden et al. | |
| 5,649,937 A | 7/1997 | Bito et al. | |
| 5,662,683 A | 9/1997 | Kay | |
| 5,667,513 A | 9/1997 | Torrie et al. | |
| 5,674,230 A * | 10/1997 | Tovey | A61B 17/0469 606/139 |
| 5,713,903 A | 2/1998 | Sander et al. | |
| 5,792,115 A | 8/1998 | Horn | |
| 5,817,054 A | 10/1998 | Grimm | |
| 5,931,869 A | 8/1999 | Boucher et al. | |
| 5,944,738 A | 8/1999 | Amplatz et al. | |
| 6,086,600 A | 7/2000 | Kortenbach | |
| 6,095,915 A | 8/2000 | Geissler et al. | |
| 6,113,609 A | 9/2000 | Adams | |
| 6,482,197 B2 | 11/2002 | Finch et al. | |
| 6,569,173 B1 | 5/2003 | Blatter et al. | |
| 6,596,013 B2 | 7/2003 | Yang et al. | |
| 6,736,828 B1 * | 5/2004 | Adams | A61B 17/00234 606/151 |
| 8,241,308 B2 | 8/2012 | Kortenbach et al. | |
| 2002/0035370 A1 | 3/2002 | Kortenbach | |
| 2002/0082621 A1 * | 6/2002 | Schurr | A61B 17/0643 606/151 |
| 2002/0156344 A1 | 10/2002 | Pasricha et al. | |
| 2003/0040761 A1 | 2/2003 | Pugsley et al. | |
| 2003/0149439 A1 | 8/2003 | Wendlandt | |

* cited by examiner

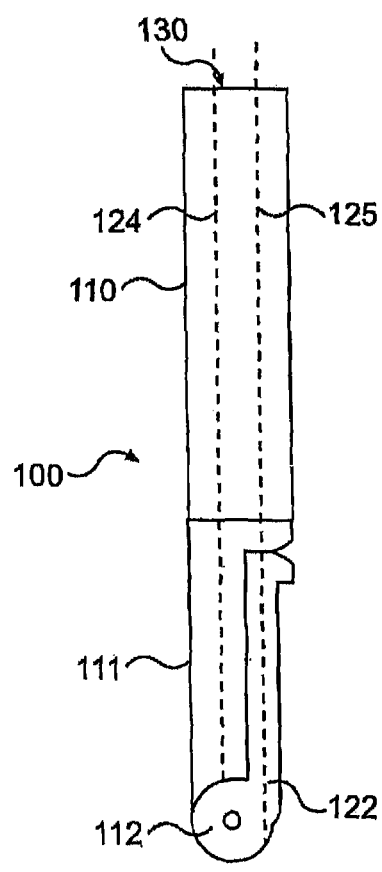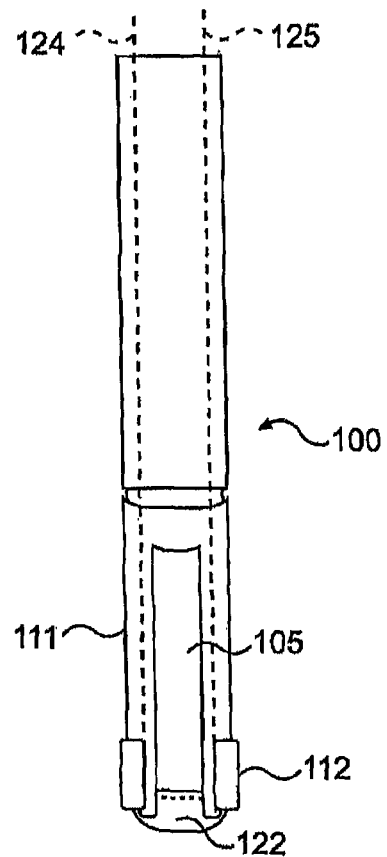
FIG. 2(a)  FIG. 2(b)

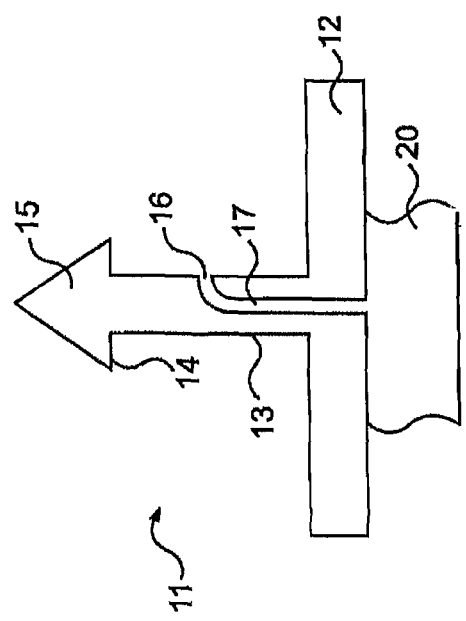
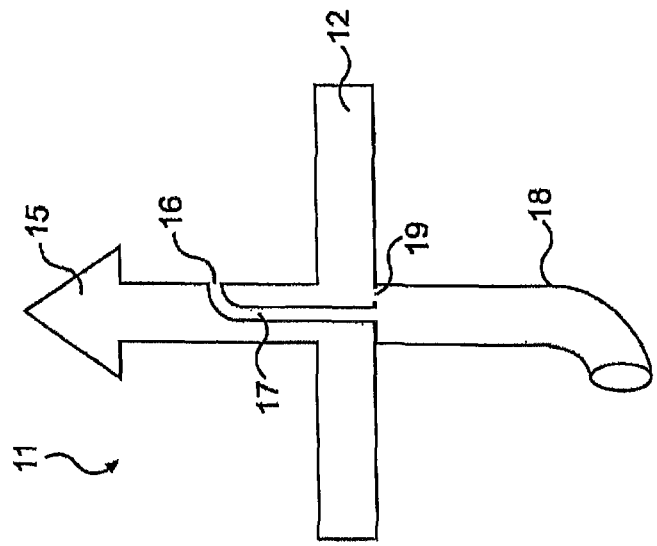
FIG. 5(a)
FIG. 5(b)

TISSUE FASTENING DEVICES AND PROCESSES THAT PROMOTE TISSUE ADHESION

CROSS-REFERENCE TO RELATED APPLICATIONS

This application is a continuation of U.S. patent application Ser. No. 13/549,392, filed on Jul. 13, 2012, now abandoned, which is a continuation of U.S. patent application Ser. No. 10/345,150, filed on Jan. 16, 2003, now U.S. Pat. No. 8,241,308, which is a continuation of U.S. patent application Ser. No. 10/128,508, filed on Apr. 24, 2002, now abandoned, all of which are incorporated herein by reference in their entireties.

FIELD OF THE INVENTION

The present invention relates to surgical fasteners and, particularly, to tissue fasteners. Still more particularly, the present invention relates to tissue fasteners that promote tissue adhesion and prevent fastener migration, especially for use in a GERD fundoplication procedure.

BACKGROUND OF THE INVENTION

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus into the stomach. This pressure essentially closes the esophagus so that contents of the stomach cannot pass back into the esophagus. The LES opens in response to swallowing and peristaltic motion in the esophagus, allowing food to pass into the stomach. After opening, however, a properly functioning LES should return to the resting, or closed state. Transient relaxations of the LES do occur in healthy individuals, typically resulting in occasional bouts of heartburn.

The physical interaction occurring between the gastric fundus and the esophagus also prevents gastroesophageal reflux. The gastric fundus is a lobe of the stomach situated at the top of the stomach proximal to the esophagus. In healthy individuals, the fundus presses against the opening of the esophagus when the stomach is full of food and/or gas. This effectively closes off the esophageal opening to the stomach and helps to prevent acid reflux back into the esophagus.

In individuals with GERD, the LES functions abnormally, either due to an increase in transient LES relaxations, decrease in length of the esophagus, decreased muscle tone of the LES during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not cure the disease completely.

A surgical procedure, known generally as fundoplication, has been developed to prevent acid reflux in patients whose normal LES functioning has been impaired, either as a result of GERD or otherwise. Fundoplication involves bringing the fundus into closer proximity to the esophagus to help close off the esophageal opening into the stomach. In Nissen Fundoplication, a particular type of the fundoplication procedure, the fundus is pulled up and around the esophagus and then sutured to itself and the esophagus such that it completely encircles the esophagus. Traditionally, this procedure has been performed as an open surgery, but has recently enjoyed success as a laparoscopic procedure, as discussed in McKernan, J. B., Champion, J. K., "Laparoscopic antireflux surgery," *American Surgeon*, Vol. 61, pp. 530-536, (1995).

As with any open surgery, complications can occur as a result of infection, blood loss or from the use of anesthesia. Further, the relatively large incisions necessary in the performance of open surgery require extended recovery times for the incision to heal. Though laparoscopic surgical procedures reduce these negative effects by using relatively small devices at a relatively small incision site in the abdominal wall, there still exists an increased risk of infection due to the incision. The location of the incision in the abdominal wall presents a risk of other negative effects, such as sepsis, which can be caused by leakage of septic fluid contained in the stomach.

Other surgical procedures specifically address the LES. These procedures attempt to prevent reflux by thickening the LES region and reducing the diameter of the esophageal opening to the stomach, i.e., tighten the LES region. However, existing procedures are lengthy and difficult to perform.

SUMMARY OF THE INVENTION

The present invention includes devices and related methods to perform an endoluminal medical procedure, especially for the treatment of GERD. In particular, the inventive devices and methods promote adhesion of tissue to be joined in, for example, an endoscopic fundoplication procedure. It is to be understood that the inventive devices, including the tissue fasteners, and methods may be used in other tissue attachment procedures, such as stomach to diaphragm, stomach to abdomen, stent or stent graft attachment, stomach plication, wound closure, soft tissue attachment and others.

To attain the advantages and in accordance with the purpose of the invention, as embodied and broadly described herein, the invention includes a surgical fastener for fastening tissue segments having tissue surfaces. The fastener includes a first fastener member having a base and a piercing element connected to the base for piercing the tissue segments to be fastened, a second fastener member having an opening for receiving and retaining the piercing element of the first fastener member such that the tissue segments to be fastened are retained between the first and second fastening members, and means for promoting adhesion between the tissue surfaces.

In a further embodiment, the opening in the second fastener member for receiving the piercing element of the first fastener member includes a hollow post. The hollow post will extend at least a portion of the length of the piercing element once the two fastening members are connected. The hollow post may have a piercing tip to facilitate its movement into the tissue layers. The hollow post may include a reservoir filled with a therapeutic agent. The agent may be released by piercing the reservoir with the first fastener member.

According to embodiments of the invention, the adhesion promoting means may include a passageway in the first fastener member. The passageway has a first end for connection to a source of an adhesion promoting substance and connects to at least one port in the first fastener member allowing delivery of the adhesion promoting substance to the tissue segments. The passageway may be in the base and the piercing element, and the port may be in the piercing element. The source of an adhesion promoting substance may include a reservoir for containing the adhesion promoting substance. The act of fastening may serve to deliver the adhesion promoting substance between the layers of tissue undergoing attachment. Alternatively, a delivery tube may be connected to the first end of the passageway for providing delivery of the adhesion promoting substance to the passageway.

In a further embodiment, the reservoir may be on the distal end of the piercing element of the first fastening member or at the opening of the second fastener member. In particular, the reservoir may be part of a hollow post serving as the opening. The act of fastening the two fastening members will further lead to a crushing, piercing, or otherwise opening of the reservoir, releasing the adhesion promoting means between the layers of the tissue undergoing attachment.

According to further embodiments of the invention, the adhesion promoting means may include a device releasably receiving one of the first and second fastening members. The device has a passageway for receiving a delivery mechanism for delivering an adhesion promoting substance to the tissue segments.

According to still further embodiments of the invention, the adhesion promoting means may be comprised of, carry, or include a filament, coating, wrapping, cuff, or other adhesion promoting material around a portion of the first fastener member for causing an adhesion in the tissue segments to be fastened.

According to another embodiment, the adhesion promoting means is sealed within the anchor. The adhesion promoting means may be contained within the piercing element of the first fastening member, within the opening of the second fastener member, or in combination of the two. In a preferred embodiment, the adhesion promoting means is sealed within the opening of the second fastening member behind a frangible septum or membrane. When the piecing element pierces the septum or membrane, the adhesion promoting means is released between the tissue layers of the tissues undergoing attachment. The use of a hollow post as the opening in the second fastening member may facilitate distribution of the adhesion promoting means between the tissue layers.

According to yet further embodiments of the invention, the adhesion promoting means may include at least one puncture member located on the base of the first fastener member. The at least one puncture member may include a spike or a blade having a height of slightly greater than the thickness of one of the tissue segments to be fastened.

In yet a further embodiment, the fastener may be designed to accept a needle delivering an adhesion promoting means between the layers of the tissues being attached. The needle may be integral to either first or second fastening member or may be delivered through either fastening member during or following attachment of the first member to the second member. The needle may extend through at least one port within one of the members. The needle directs the injection of an adhesion promoting means between the layers of the tissues being attached. The needle may be independent of but deliverable in conjunction with the fasteners and fastening tool. The needle permits a controlled volume and flow of adhesion promoting means to the tissues. The needle may be placed in more than one injection site, successively by use of more than one exit port within the fastening members. The needle may have more than one head to increase the area of the injection site. The needle may be a bundle of needles delivered together and having various injection sites between the tissue layers.

According to further aspects, the invention includes a method of fastening surfaces of tissue segments. The method includes the steps of piercing the tissue segments to be fastened with a first part of a tissue fastener, receiving the first part of the tissue fastener in a second part of the tissue fastener thereby retaining the tissue segments to be fastened between the first and second parts of the tissue fastener, and delivering an adhesion promoting substance to the interface between the surfaces of the tissue segments to be joined.

According to embodiments of the invention, the delivering step includes delivering the adhesion promoting substance through a passageway in the first part of the tissue fastener. The passageway has a first end for connection to a source of an adhesion promoting substance, and the passageway connects to at least one port in the first part allowing delivery of the adhesion promoting substance to the tissue segments.

According to embodiments of the invention, delivering the adhesion promoting substance may include compressing a reservoir that contains the adhesion promoting substance. According to other embodiments, delivering the adhesive promoting substance may include piercing a reservoir that contains the adhesion promoting substance. According to other embodiments, delivering the adhesion promoting substance includes delivery of the adhesion promoting substance to the passageway by a delivery tube connected to the first end of the passageway. According to yet other embodiments, the adhesion promoting substance may be delivered through a passageway in a device that releasably receives one of the first part and second part.

According to further aspects, the invention includes a device for promoting adhesion of a first segment of lower esophageal sphincter tissue and a second segment of fundus tissue. The device includes an elongate body configured for insertion into the esophagus, an element connected to and pivoting from a distal end of the elongate body, the element having a retracted position along an axis of the elongate body and an extended position at an angle to the axis, and means associated with at least one of the elongate body and the element for promoting adhesion of the first and second tissue segments.

According to further embodiments of the invention, the means for promoting adhesion includes means for causing trauma to the first and second tissue segments. The trauma causing means may include at least one puncture element located on at least one of the element and the elongate body.

According to still further aspects, the invention includes a surgical fastener for fastening tissue segments having tissue surfaces. The fastener includes a first fastener part including a base and a plurality of barbs extending from the base, and a second fastener part including a mesh screen defining a plurality of holes for receiving the plurality of barbs. The mesh screen or the barbs may include any of the adhesion promoting means mentioned within this disclosure.

According to additional aspects, the invention includes a device for fastening a first segment of lower esophageal sphincter tissue to a second segment of fundus tissue. The device includes a fastener having a first fastener part and a second fastener part. The device also includes an elongate body configured for insertion into the esophagus. The distal end of the elongate body is configured to hold one of the first fastener part and the second fastener part. The device further includes an element connected to and pivoting from the distal end of the elongate body. The element has a retracted position along an axis of the elongate body and an extended position at an angle to the axis. The element is configured to hold the other of the first fastener part and the second fastener part. The device also includes a mechanism capable of reciprocating within a channel of the elongate body and urge the first and second fastener parts together. In an embodiment, the first fastener part may include a base and a plurality of barbs extending from the base, and the second fastener part may include a mesh screen defining a plurality of holes for receiving the plurality of barbs.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIGS. 2(a)-2(c) are a respective side view of an exemplary endoscopic fundoplication device with a grasping arm in a closed position and a front view and a side view of the device with the grasping arm in an open position.

FIG. 5(a) is a sectional side view of one part of a tissue fastener, according to an embodiment of the present invention.

FIG. 5(b) is a sectional side view of one part of another tissue fastener, according to an embodiment of the present invention.

DESCRIPTION OF THE EMBODIMENTS

Reference will now be made in detail to the present embodiments the invention, examples of which are illustrated in the accompanying drawings. Wherever possible, the same reference numbers will be used throughout the drawings to refer to the same or like parts.

A newly developed form of fundoplication, referred to as endoscopic fundoplication, is an endoluminal procedure in which the fundus wall is folded back onto the esophagus wall. The tissue fold formed between the esophagus and the fundus then is secured. Endoscopic fundoplication is intended to be performed as an endoluminal procedure in which insertion of required medical instruments occurs through the esophagus. Such a procedure has the benefits of being less invasive, quicker, and less expensive as compared to previous techniques.

Figure 1:
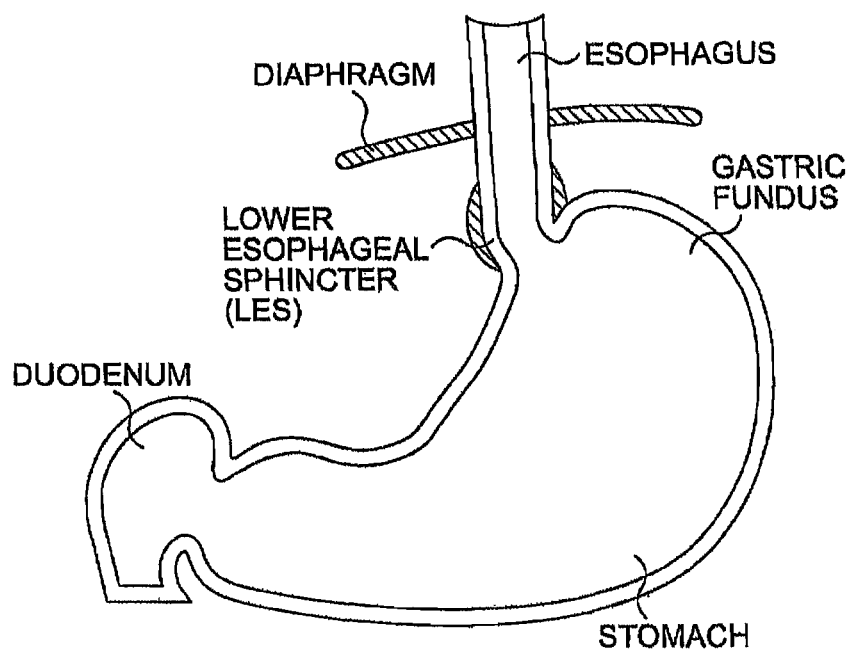
FIG. 1 is a cross-sectional view of the gastrointestinal tract from a mid-point of the esophagus to a point near the beginning of the duodenum.
Figure 2C:
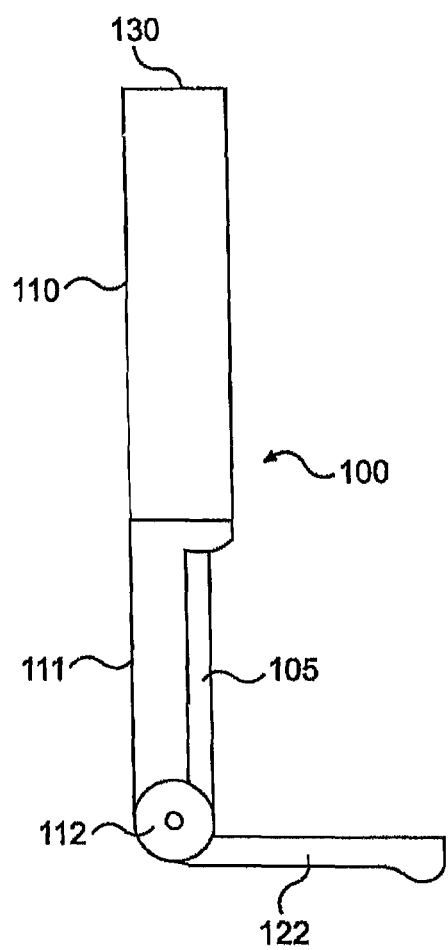
Figure 2D:
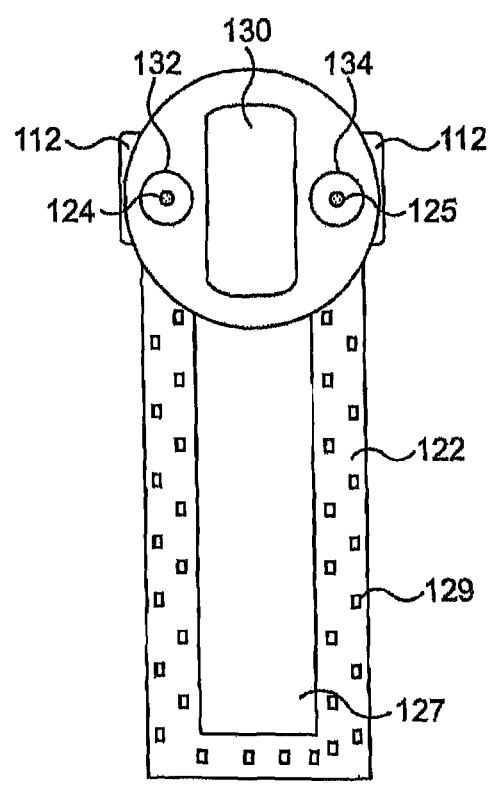
FIG. 2(d) is a top view of the device of FIGS. 2(a)-2(c), with the grasping arm in an open position.

An exemplary device employed in endoscopic fundoplication is shown in FIGS. 2(a)-2(d). This device, referred to as an A-frame grasper-overtube 100, includes an overtube 110 and a distal A-frame head 111 attached to the overtube 110 by any suitable means, such as a set screw and a steel ring within the device for the screw to attach with. A-frame head 111 includes a cable-actuated grasper at a distal end of the device. The cable-actuated grasper includes a grasping arm 122 attached to the distal end of A-frame head 111 by a pivot 112. Overtube 110 includes a lumen 130, preferably having a diameter capable of accommodating an endoscope in the diameter range of 6 to 10 mm., preferably 6 mm., as well as other endoluminal devices. This range of endoscope sizes is not meant to be limit the possible endoscope size to be used in connection with this invention. Lumen 130 extends into A-frame head 111. Overtube 110 is preferably made of metal reinforced plastic and is flexible. At its distal end, near grasping arm 122, A-frame head 111 includes a large opening 105 disposed in a sidewall of A-frame head 111. Opening 105 accommodates grasping arm 122 such that, in an insertion position of the grasper-overtube 100, grasping arm 122 essentially closes opening 105 and lies substantially flush with the rest of the A-frame sidewall that defines opening 105. As shown in FIG. 2(d), grasping arm 122 also includes an elongated slot or opening 127 extending substantially longitudinally in the center of the arm and may include a plurality of protrusions 129 for assisting in grasping the tissue.

The insertion or closed position of grasper-overtube 100 is shown best in FIG. 2(a). Grasping arm 122 of grasper-overtube 100 may be actuated or opened by pulling a first cable 124 attached at the proximal end of grasping arm 122 at or adjacent pivot 112 and running up through a lumen 132 in overtube 110 to a proximal end of the device. The pulling motion of first cable 124 causes grasping arm 122 to rotate about pivot 112 to thereby form an increasing angle between grasping arm 122 and the reminder of A-frame head 111. FIG. 2(c) shows grasping arm 122 in an actuated or open position and forming approximately a 90 degree angle with the reminder of A-frame head 111. The angle of the A-frame grasping arm during delivery of the device is preferably approximately 0 degrees, or straight upward. The angle may also be approximately 180 degrees, or straight downward, as desired. The angle of the A-frame grasping arm during clamping of tissue segments is preferably approximately 0 degrees, and will accommodate tissue thickness. A second cable 125 also may be attached at the proximal end of grasping arm 122 and run through a lumen 134 in overtube 110 to a proximal end of the device. Second cable 125 is actuatable to rotate grasping arm 122 from an open position to a closed position. Pulling of second cable 125 causes grasping arm 122 to rotate about pivot 112 in a direction opposite that caused by pulling on first cable 124, and thus reducing the angle formed between grasping arm 122 and the reminder of A-frame head 111 toward the completely retracted position shown in FIG. 2(a). First and second cables 124, 125 may run through a combined or separate channels 132, 134 formed in overtube 110 and extend from a proximal end to a distal end of the device. Alternatively, one cable may extend from a proximal end of overtube 110, connect to grasping arm 122, loop around pivot 112, and extend back to the proximal end of overtube 110. In this arrangement, the cable would have two proximal ends and pulling one end of the proximal ends of the cable would cause retraction of the grasping arm 122, and pulling the other proximal end of the cable would cause opening of the grasping arm 122.

A-frame head 111 may include a clear section or opening formed opposite opening 105. Clear section or opening would allow for visual confirmation of the location of tissue intended to be folded by grasper-overtube 100. Such visual confirmation could be achieved by way of, for example, an endoscope. Alternatively, the whole A-frame head 111 may be fabricated of a clear material. In an alternate embodiment, the fastening device is delivered directly through the endoscope without the use of grasper-overtube 100. This approach would allow for the highest level of visualization.

Using the grasper-overtube shown in FIGS. 2(a)-2(d), endoscopic fundoplication is performed in the following manner. In the insertion position shown in FIG. 2(a), grasper-overtube 100 is inserted into the stomach through the esophagus. Insertion of grasper-overtube 100 continues until the distal end of the grasper-overtube 100 reaches a point within the stomach below the fundus. Grasper-overtube 100 preferably is inserted with the sidewall containing opening 105 facing toward the fundus. However, it is contemplated that after insertion, grasper-overtube 100 can be rotated about its longitudinal axis to the desired position. An endoscope may be extended through lumen 130 in overtube 110 to provide vision within the stomach during insertion of grasper-overtube 100. The endoscope may also be delivered into the esophagus before or after the overtube. Preferably, a 6 to 10 mm. diameter articulating endoscope is used, however the size and type of endoscope can be selected depending on the particularities associated with the procedure being performed.

Figure 3A:
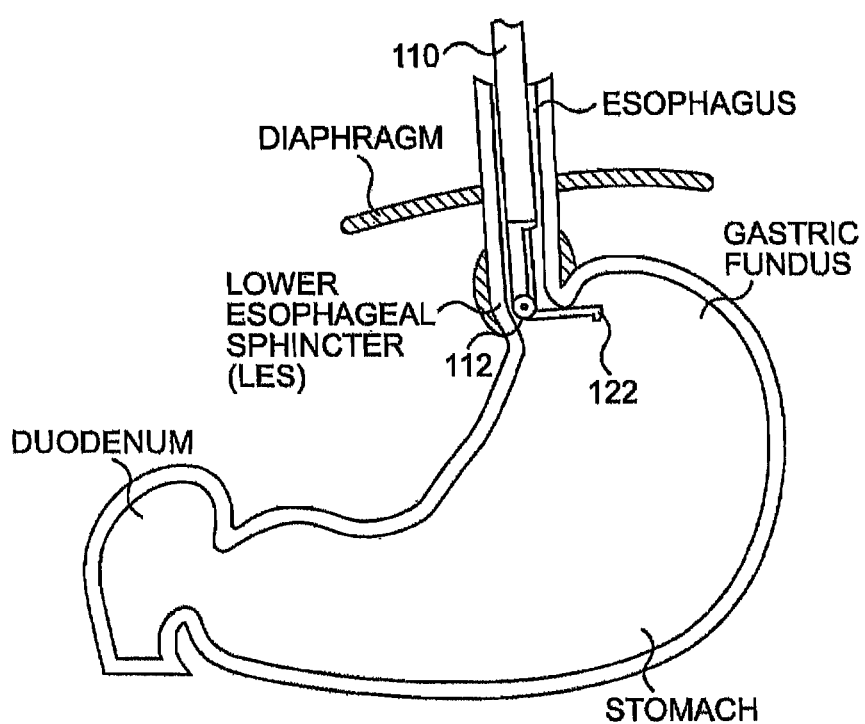
FIG. 3(a) is a cross-sectional view of a portion of the esophagus and stomach with the device of FIGS. 2(a)-2(d) inserted to perform a fundoplication procedure.
Figure 3B:
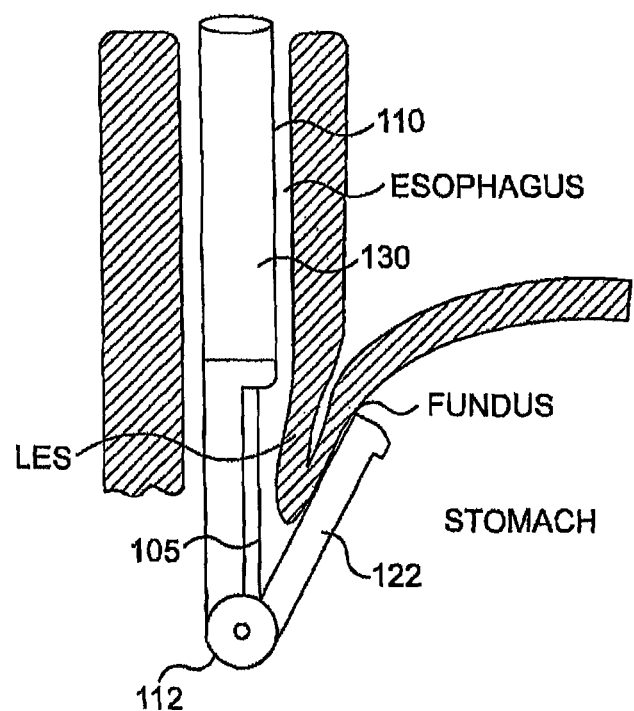
FIG. 3(b) is a cross-sectional view of a portion of the esophagus and stomach with the device of FIGS. 2(a)-2(d) activated to fold the fundus wall onto the esophagus wall during a fundoplication procedure.

After inserting and positioning overtube 110 to the desired location below the fundus, grasping arm 122 is actuated and pivots downward to its open position between 180 and 90 degrees to the reminder of A-frame head 111, as shown in FIG. 3(a). It may be desirable to then grasp a portion of the stomach or fundus wall and pull this portion of the wall downward, to invaginate the stomach wall relative to its natural position. Such grasping may be performed by virtue of a grasping surface on the A-frame or by delivery of a grasping device, such as forceps or a suction device, through the overtube and to the stomach wall. Grasper-overtube 100 is then lifted upward toward the opening of the esophagus' in the stomach. Next, cable 124 is actuated to return grasping arm 122 to its closed position. The arcing motion of grasping arm 122 as it engages the wall of the fundus, causes the fundus to fold against the side of the esophagus near its opening into the stomach, as illustrated in FIG. 3(b). After the fundus wall has been folded back onto the esophagus wall, the fastening mechanism is delivered to the tissues to be attached. The fastening mechanism is aligned with the site of fastening, and the fasteners are delivered. The adhesion promoting means is actuated either by the action of applying the fasteners or by a successive application of an adhesion promoting means, as will be described further herein. Once the fastener or fasteners have been delivered to the tissues and the tissues are secured in place, grasper-overtube 100 is removed.

FIGS. 2(a)-2(d) are meant to show one exemplary device and actuation mechanism for an exemplary fundoplication procedure described in connection with FIGS. 3(a)-3(b). Other devices and actuation mechanisms known to those in the art of endoscopic medical devices may be used. As examples only, actuation mechanisms that incorporate vacuum, hydraulics, linkages, and/or cams may be used.

After the fold has been created, securing the fundus can be accomplished using a variety of fastening mechanisms and/or methods, examples of which will be described below. The grasper-overtube and fundoplication procedure just described are exemplary of a device and procedure used with the fasteners and methods to promote tissue fastening and adhesion according to the present invention. It is desirable that the fastening mechanisms and/or methods according to the present invention can be installed or performed relatively quickly in a relatively non-invasive manner, and can create a substantially uniform fold of tissue once installed. It is also desirable that those mechanisms and/or methods cause adhesion of the tissue joined in the fundoplication procedure.

The present invention therefore is directed to fasteners and methods especially suitable to fasten tissue and promote adhesion of that tissue in an endoscopic fundoplication procedure. The fasteners described in detail below include mechanisms and methods for delivering an adhesion promoting component to the interface of the tissue segments to be joined, mechanisms and methods for promoting tissue adhesion in the tissue segments to be joined through, for example, mechanical trauma, and mechanisms and methods for preventing fastener, migration. Although the fasteners and methods according to the present invention are especially suitable for use in an endoscopic fundoplication procedure, those in the medical arts will understand that the fasteners and methods may be suitable for other endoscopic and non-endoscopic surgical applications requiring the adhesion of tissue segments. These may include tissue attachment procedures such as stomach to diaphragm, stomach to abdomen, stent or stent graft attachment, stomach plication, wound closure, soft tissue attachment and others.

Figure 4A:
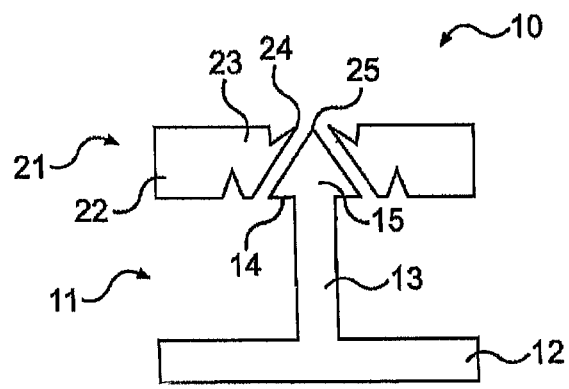
FIG. 4(a) is a sectional side view of an exemplary tissue fastener for use in an endoscopic fundoplication procedure, according to an embodiment of the present invention.
Figure 4B:
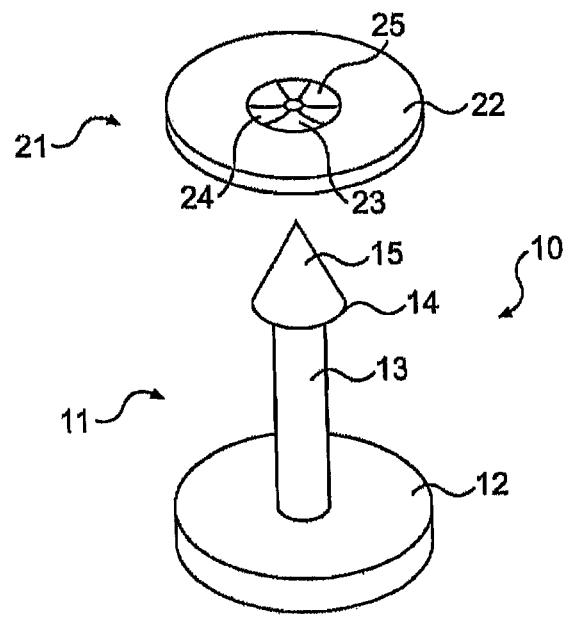
FIG. 4(b) is a perspective view of the fastener shown in FIG. 4(a).

FIGS. 4(a) and 4(b) show an exemplary tissue fastener 10 for use in a fundoplication procedure, according to the present invention. Fastener 10 has a first fastening member or part 11 and a second fastening member or part 21 for retaining first part 11. First part 11 includes a base 12 and a shaft 13 having a spike 15 for piercing tissue and for fastening to second part 21. Second part 21 has an outer annular portion 22, an inner annular portion 23, and an opening 25 through which spike 15 of first part 11 may pass. Inner portion 23 has projections 24 and has a weakened structure permitting passage of spike 15. After spike 15 of first part 11 has been inserted through opening 25 in second part 21, projections 24 on second part 21 contact an edge 14 on spike 15 preventing spike 15 from passing back through opening 25. In this way, first part 11 and second part 21 remain fastened together.

While fastener 10 is shown having a generally annular shape, it should be recognized that other suitable shapes, such as rectangular or square, are within the scope of the invention. Preferably, the compliance of the material used to form the fasteners is similar to that of the esophageal and stomach tissue, however any biocompatible compliance will do. Moreover, the size of fastener 10 may vary.

To fasten two pieces of tissue together using fastener 10, spike 15 of first part 11 pierces the two tissue segments to be joined, such as the LES and the fundus, and passes through opening 25 in second part 21, thereby retaining the two tissue segments between first part 11 and second part 21. First part 11 and second part 21 can be made from any suitable biocompatible material, such as an implantable grade plastic, and also may be bioabsorbable. Suitable materials include stainless steel (316 SS), nitinol, titanium, shape memory polymers such as polynorbene, polyethylene, PLLA, PGA, polyurethane, and PTFE, ceramics, and compositions of materials such as a metal and a polymer or a filled polymer.

Any suitable mechanism, such as a surgical stapling mechanism or a surgical fastening system, for delivering fastener 10 to the site of the LES and gastric fundus, and then fastening parts 11 and 21 together, may be used. Examples of such suitable devices are shown and described in U.S. Pat. Nos. 6,113,609 and 6,086,600, the entire disclosure of which is incorporated by reference herein. These patents describe exemplary, suitable devices and methods for mounting and releasing the fastener parts from the device.

Figure 2E:
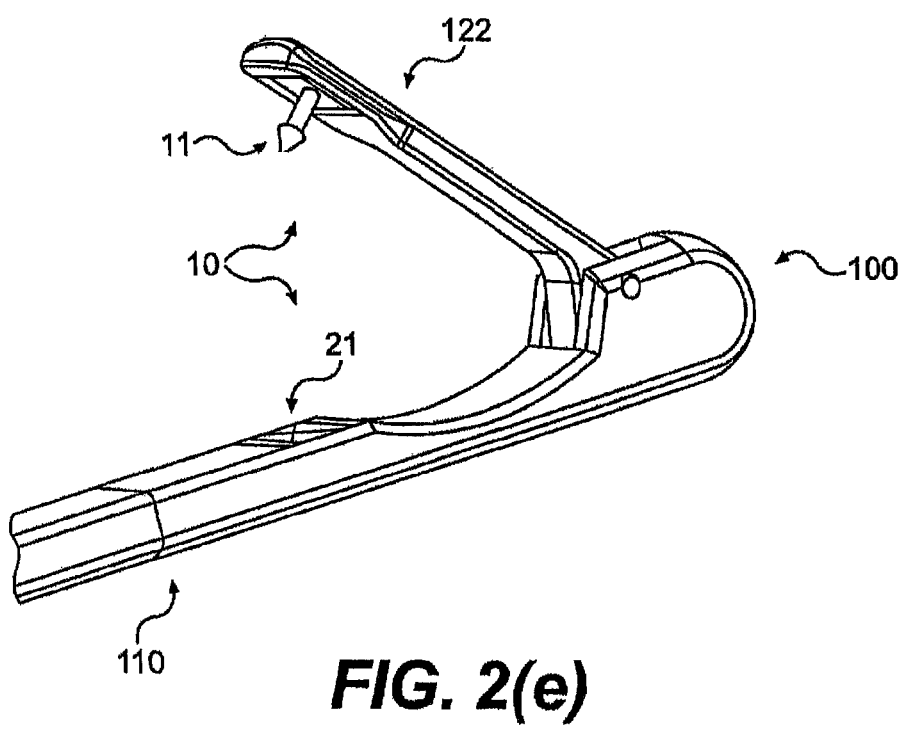
FIG. 2(e) is a perspective view of an exemplary tissue fastener insertion device, for use in an endoscopic fundoplication procedure, with a grasping arm in an open position.
Figure 4C:
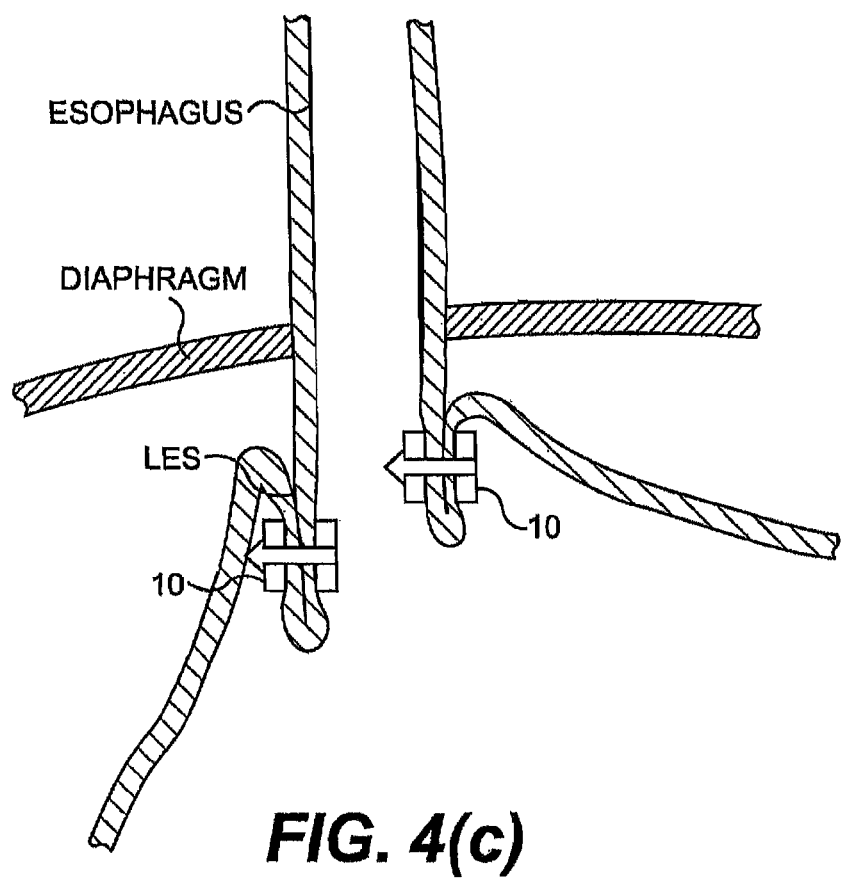
FIG. 4(c) is a partial cross-sectional view of the esophagus and the stomach, with the LES and fundus fastened together after a fundoplication procedure.

The delivery mechanism used to deliver and fasten fastener 10 also may be used in combination with, or may be a portion of, the grasper-overtube 100 described in connection with FIGS. 2(a)-2(d). For example, the grasper-overtube may be modified, as shown in FIG. 2(e), so that part 11 is associated with the actuating arm 122 and part 21 is associated with the main body 110 of the device. Grasper-overtube may then function like a stapling mechanism. When the actuating arm swings toward the body of the device, parts 11 and 21 fasten together. FIG. 4(c) shows tissue fasteners fastening the LES and gastric fundus in a fundoplication procedure. FIG. 4(c) shows two fasteners 10 at opposite sides of the LES. More or less fasteners may be used, as deemed suitable for the particular procedure. The delivery mechanism may include a piercing mechanism to pierce the tissue segments to be fastened together.

Figure 5C:
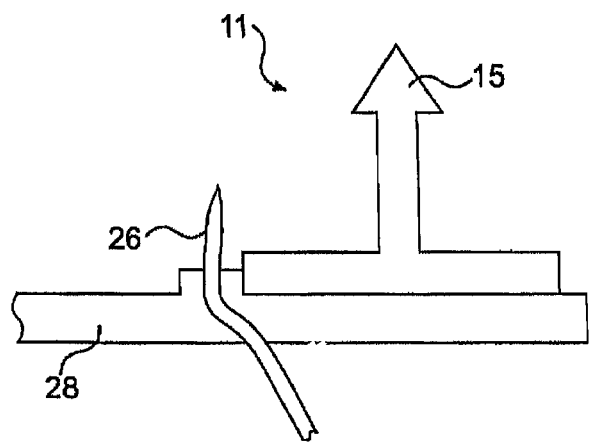
FIG. 5(c) is a sectional side view of one part of a tissue fastener and a tissue fastener insertion device, according to an embodiment of the present invention.
Figure 5D:
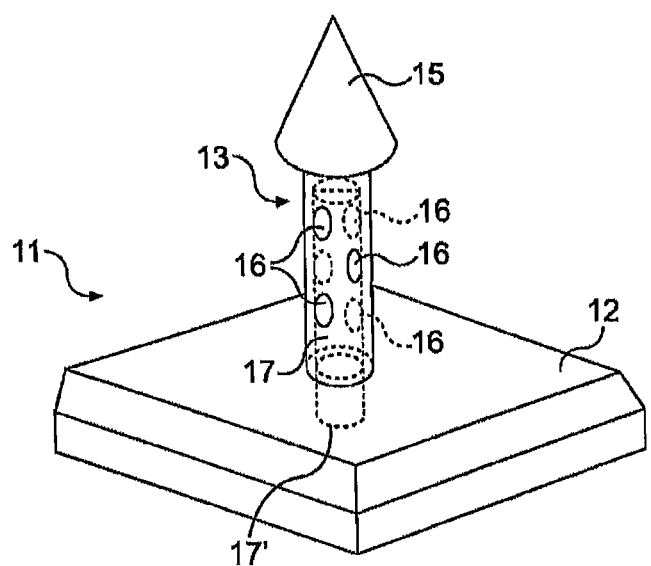
FIG. 5(d) is a perspective view of one part of a tissue fastener, according to another embodiment of the present invention.
Figure 5E:
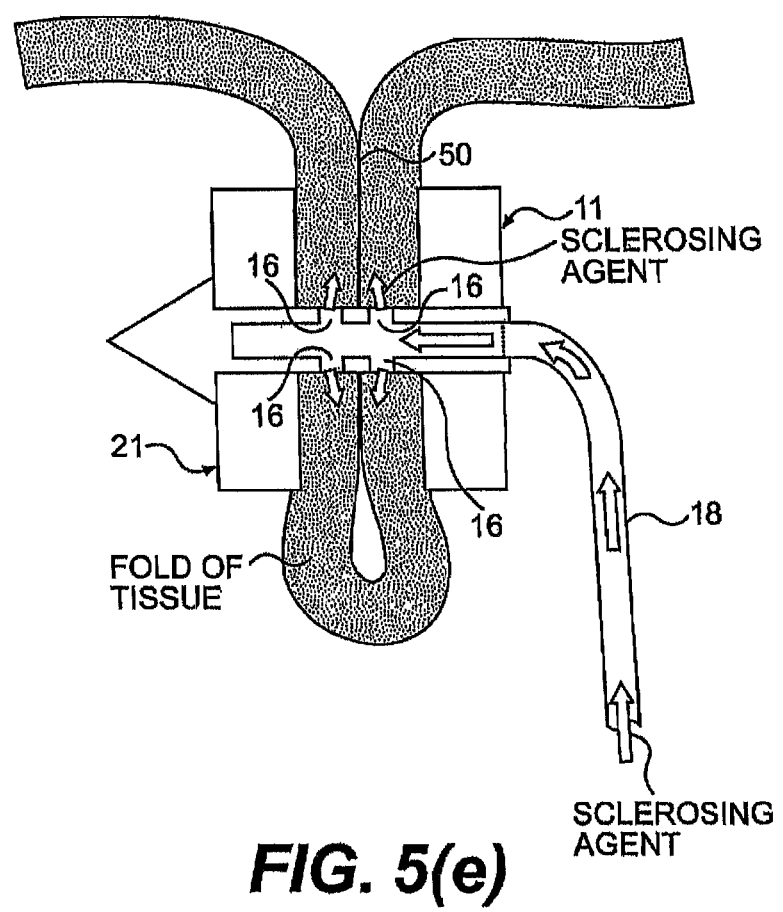
FIG. 5(e) is a partial cross-sectional view of a tissue fold secured by the fastener of FIG. 5(d), showing delivery of an adhesion promoting substance, according to an embodiment of the present invention.
Figure 5F:
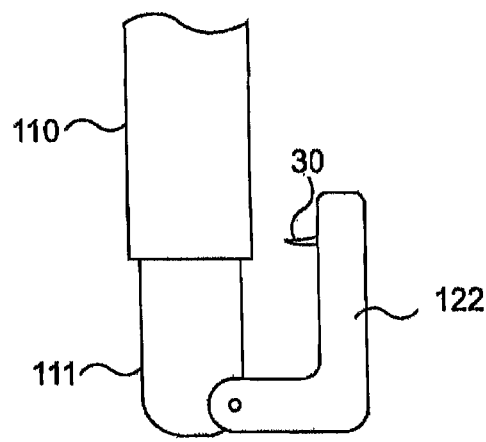
FIG. 5(f) is a sectional side view of another tissue adhesion promotion device, including a needle for adhesion promotion injection, according to an embodiment of the present invention.
Figure 5G:
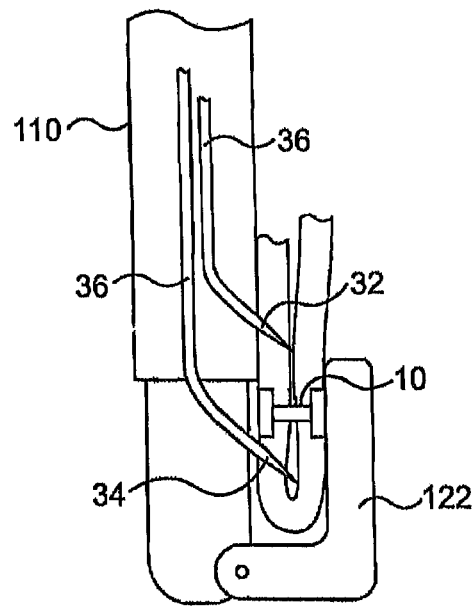
FIG. 5(g) is a sectional side view of another tissue adhesion promotion device, including multiple needles for adhesion promotion injection, according to an embodiment of the present invention.
Figure 5H:
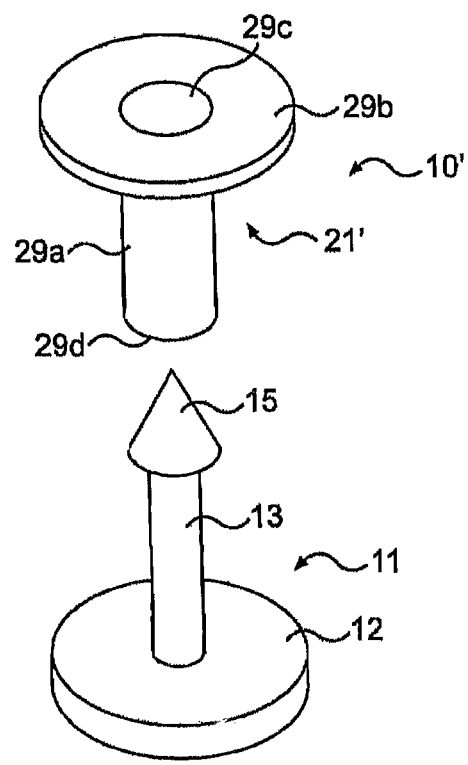
FIG. 5(h) is a side elevation view of another exemplary tissue fastener for use in an endoscopic fundoplication procedure, according to an embodiment of the present invention.

According to one embodiment of the present invention, fastener 10 also includes means to promote tissue adhesion. In the embodiment shown in FIG. 5(a), first part 11 may have a port 16 for delivering a therapeutic agent, such as a sclerosing agent, that will promote adhesion between the joined tissue segments, i.e. the LES and fundus. Over time, tissue at the tissue fold interface may be irritated by the sclerosing agent. During the healing process, the tissue in the fold interface forms adhesions strong enough to maintain the fold without the fastener. At the same time, if the fastener is made of biodegradable/bioabsorbable material, the fastener will dissolve, leaving the tissue fold intact. Other drugs and substances, both therapeutic and diagnostic, could be administered, including, for example, fibrin glue, antibiotics (such as tetracycline), anti-inflammatory agents, local anesthetics, sclerosing agents, a growth factor, a tissue irritant, a solution including a biocompatible material, a gene, a protein, an enzyme, a cell, body fluids such as blood, epoxies, biological materials, gelatin, talc, sodium morrhuate, quinacrine, bleomycin, *corynebacterium parvum*, bulking agents such as alginate and histoacryl, and adhesives (including energy activated adhesives). An example of a suitable adhesive is an adhesive sold by Cryolife under the trade name BioGlue®.

Port 16 may be located at the juncture (fold) between the two tissue segments when first part 11 and second part 21 are connected in order to provide the therapeutic agent to the interface of the adjacent surfaces of the joined tissue segments. Thus, the location of port 16 can be selected based on the thickness of the tissue segments.

As shown in FIG. 5(*a*), the therapeutic agent, such as an adhesion promoting substance, may be delivered to port 16 through a passageway 17 in first part 11. The adhesion promoting substance may be delivered from a reservoir 20 to first part 11 and passageway 17. Reservoir 20 may be crushable in order to advance the adhesion promoting substance from the reservoir, and through the passageway and port to the tissue fold. Reservoir 20 may be crushed by the delivery device during delivery of fastener 10. Reservoir 20 may be separate from or integral with either first or second parts 11,21. Reservoir 20 preferably is positioned so that it is crushed during insertion of first part 11 into second part 21.

Alternatively, as shown in FIG. 5(*b*), the adhesion promoting substance may be delivered to passageway 17 in first part 11 with a syringe (not shown) or other similar lumen or mechanism associated with the fastener delivery device. To facilitate the delivery of the adhesion promoting substance, first part 11 may include a delivery tube 18 connected to a syringe or other delivery mechanism. Delivery tube 18 may be permanently or temporarily connected to first part 11. Preferably, a temporary connection is provided by a frangible interlace 19 located between delivery tube 18 and first part 11 to allow delivery tube 18 to be removed after the desired amount of adhesion promoting substance has been delivered to the tissue segments to be joined.

FIG. 5(*d*) shows another embodiment of tissue fastener part 11. Part 11 includes multiple sidewall ports 16 along shaft 13. Ports 16 are in fluid communication with passageway 17 within shaft 13. Passageway 17, in turn, is in fluid communication with an entrance hole 17' in the bottom of base 12. Multiple ports may be used to obtain even distribution of the adhesion promoting substance.

Once fastener 11 of FIG. 5(*d*) is in place to secure the fold of tissue of the LES and fundus, an adhesion promoting agent may be injected into passageway 17 and through ports 16, as shown in FIG. 5(*e*). The agent may be injected through a drug delivery tube 18 contained within the fastener delivery and fastening device. The drug delivery tube may be connected to a reservoir of adhesion promoting agent at the proximal end of the delivery and fastening device. The agent will proceed out of ports 16 and into the tissue fold interface (designated by reference numeral 50) and produce adhesions, as discussed above.

As an alternative, and as shown in FIG. 5(*c*), an injection needle tip 26 may be inserted through a passage 27 in a tissue fastener insertion device shown generally at 28. Injection needle tip 26 may advance into the tissue pieces to be joined, proximate spike 15 of fastener 10. After the desired amount of adhesion promoting substance (such as sclerosing agent) has been delivered, injection needle tip 26 may be removed. Passage 27 and its associated injection needle may be integral with fastener insertion device 28, so that passage 27 extends through device 28 to a proximal end where a syringe or other suitable mechanism delivers the adhesion promoting substance. As an alternative, the injection needle may be delivered to the tissue through an endoscope or other delivery mechanisms.

FIG. 5(*f*) shows the distal end of an overtube 110 and an A-frame head 111 at the distal end of overtube 110. A needle 30 extends from grasping arm 122 proximate the position that A-frame head 111 holds and fastens a tissue fastener. Needle 30 may communicate with a passage (not shown) that extends within grasping arm 122 to the remainder of the A-frame head 111, through overtube 110, and to the proximal end of the fundoplication device. At the proximal end, a syringe or other suitable mechanism delivers an adhesion promoting substance to the passage leading to the needle.

In addition to or as an alternative to a needle extending from grasping arm 122, a needle may extend through the opposite side of the fundoplication device, i.e., through a side of overtube 110 or the main portion of A-frame head 111. In addition, needle injection may occur at more than one site. As shown in FIG. 5(*g*), a needle 32 protrudes from a side of overtube 110 just proximal to the site of fastener insertion, and a needle 34 protrudes from a side of the main portion of A-frame head 111 just distal to the fastener insertion site. Each needle 32, 34 may have its own corresponding passage 36 leading to the proximal end of the device, as shown in FIG. 5(*g*), or needles can share passages.

In an alternate embodiment, using embodiments shown in for example FIGS. 5c, 5d, 5e, 5f, and 5g, the adhesion promoting agent is delivered to the tissues prior to fastener placement or following fastener placement. For example, needle 26 may extend through the base of fastening member 11 as shown or into piercing element 15. Passageways such as passageway 17 and sideports such as ports 16 of FIG. 5(*d*) may be used to guide the needle or adhesion promoting substance to an area between the tissue layers. In a further embodiment, needle 26 may have more than one head, to deliver the adhesion promoting substance over a larger area. Needle 26 may also comprise a bundle of smaller needles, capable of injecting the adhesion promoting substance to multiple location at once.

Fastener 10 also may be porous, rough textured (pits or bumps), or coated with a biocompatible substance to promote adhesion and tissue ingrowth. Such substance includes collagen, carbon, diamond-like coatings, and hydroxy apetite, but this list is not meant to limit the list of coating that may improve the tissue adhesion and or tissue ingrowth capabilities of the fastener. If hydroxy apetite is utilized, a preferred method of application would be via flame spraying and the fastener would preferably comprise a material that could withstand this process, such as metals or ceramics.

FIG. 5(*h*) shows an alternate embodiment of a tissue fastener 10'. In this embodiment, fastener 10' includes a first part 11 like that of other embodiments described in this disclosure. Second part 21' of fastener 10' includes a hollow post 29a extending from a base 29b. Base 29b defines an opening 29c therein. Post 29a and opening 29c are configured to accept spike 15 and shaft 13 of first part 11. Post 29a may extend at least a portion of the length of shaft 13 once first and second parts 11, 21' are connected. Post 29a may have a piercing tip or sharp edge 29d to facilitate its movement into the tissue layers. A crushable, piercable, or otherwise frangible reservoir containing tissue adhesion promoting substance may be part of post 29a, and particularly part of the opening of post 29a into which spike 15 extends and pierces. The act of fastening the two parts 11, 21' will crush, pierce, or otherwise break open the reservoir, releasing the adhesion promoting means between the layers of the tissue undergoing attachment. It is to be understood that aspects of other tissue fastener embodiments described in this disclosure may be incorporated into the embodiment of FIG. 5(*h*). For example, an adhesion promoting substance may be delivered to a port 16 through a passageway in the first part 11, as shown and described in connection with FIG. 5(*a*).

Figure 6:
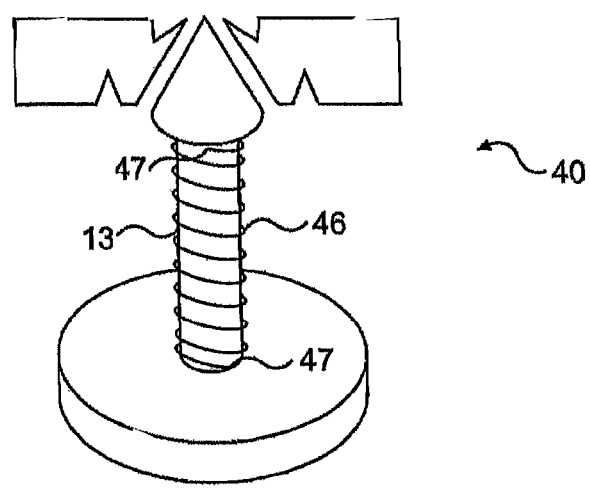
FIG. 6 is partial sectional side elevation view of another tissue fastener, according to an embodiment of the present invention.
Figure 7:
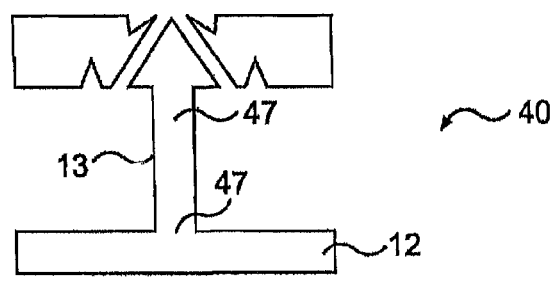
FIG. 7 is a sectional side view of the tissue fastener of FIG. 6.

In an alternate embodiment shown in FIG. 6, the adhesion promoting means may include a filament material 46 wound about the shaft 13 of a fastener 40 to promote tissue ingrowth between layers of the tissues to be joined. Alternatively, filament 46 may be a coating, wrapping, cuff or other tissue ingrowth promoting or adhesion promoting material. Fastener 40 is essentially identical to the fastener described within FIGS. 4 (*a*) and 4(*b*), with the exception of material 46 that promotes the adhesion of tissue layers as they heal. The adhesion promoting material may promote adhesion of the tissues to one another as well as to the fastener. The filament material 46 may be made from, for example, PGA, silk, stainless steel, titanium, nitinol, or any other suitable material. As shown in FIGS. 6 and 7, shaft 13 may be provided with openings 47 for anchoring filament material 46 to the shaft. Other materials may be attached to the shaft of the fastener by any of the means known in the art, including, but not limited to, adhesives, melting, spray deposition, on top of a tie layer or co-extrusion.

Figure 8:
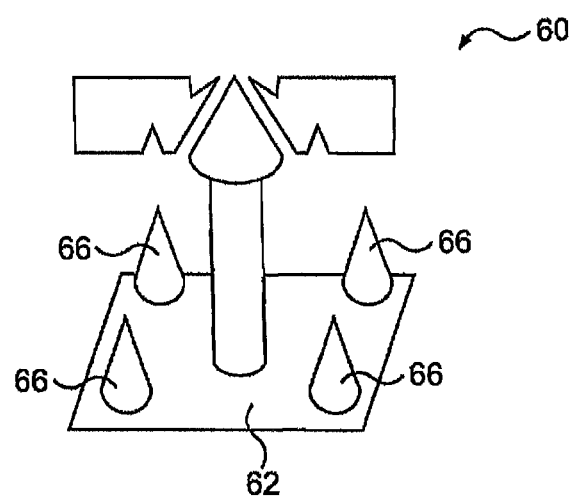
FIG. 8 is a partial sectional side elevation view of another tissue fastener, according to an embodiment of the present invention.
Figure 9:
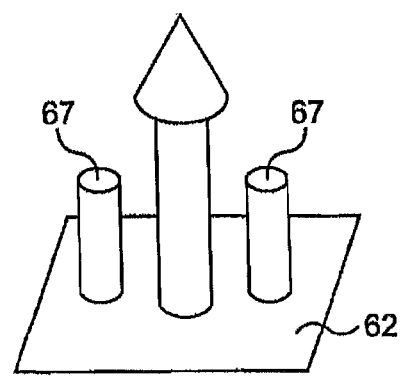
FIG. 9 is a side elevation view of one part of another tissue fastener, according to an embodiment of the present invention.
Figure 10A:
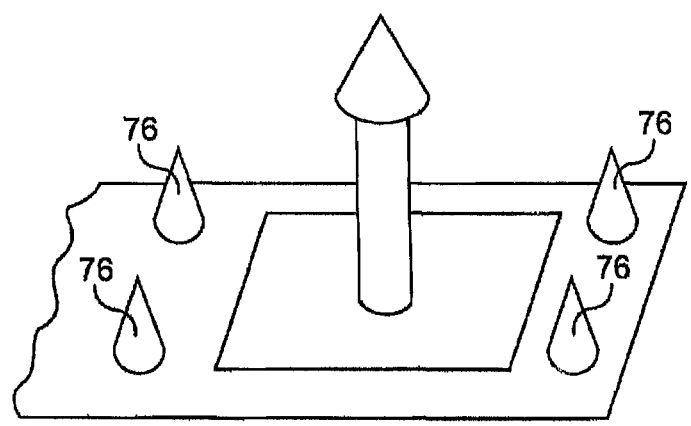
FIG. 10(a) is a side elevation view of one part of another tissue fastener and tissue fastener insertion device, according to an embodiment of the present invention.
Figure 10B:
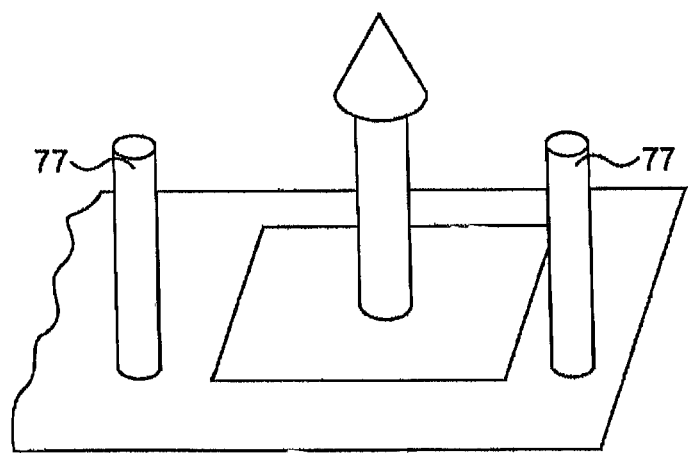
FIG. 10(b) is a side elevation view of one part of another tissue fastener and tissue fastener insertion device, according to an embodiment of the present invention.

In further embodiments of the invention, tissue adhesion is caused in the joined tissue by means other than by delivering an agent to the tissue fold. These methods include mechanical trauma (abrasion, puncturing, and others) and other like means for causing tissue trauma which will promote tissue adhesions to form between the layers of the folded tissues. As the tissues heal, they cause adhesions either by growing together or by the adhesive qualities of biological materials created by the trauma. FIGS. 8 through 10(*b*) illustrate how tissue layer trauma may be induced by mechanical means.

In the embodiments of FIGS. 8 and 9, fastener 60 includes a base 62 with spikes 66, as shown in FIG. 8, or blades 67, as shown in FIG. 9. Other suitable puncturing or cutting means may be used. When fastener 60 is installed, spikes 66 or blades 67 cause trauma to the tissue layers to be joined at the point of juncture. The traumatized cells and bleeding during the healing process form adhesions and join together. Preferably, when used in a fundoplication procedure, the spike or blade should pierce through the thickness of the stomach or esophageal wall plus a small thickness of the second tissue layer or an additional approximately one millimeter. This will cause bleeding and promote fusing of the tissue together.

Alternatively, the trauma causing means may be placed on a tissue fastening device, as shown in FIGS. 10(*a*) and 10(*b*). These Figures respectively show puncturing structure, e.g. spikes 76 or blades 77, placed on, for example, the grasping arm of the fastening device shown in FIG. 2(*e*). As the fastener is installed, spikes 76 or blades 77, which are preferably adjacent and proximate to at least one of the fastener parts, cause trauma to the tissue to be joined. The traumatized cells at the tissue layer juncture will form adhesions during the healing process and join together. It is to be understood that the mechanical trauma causing means of these embodiments also may be placed on the main body of the fastening device.

Figure 11:
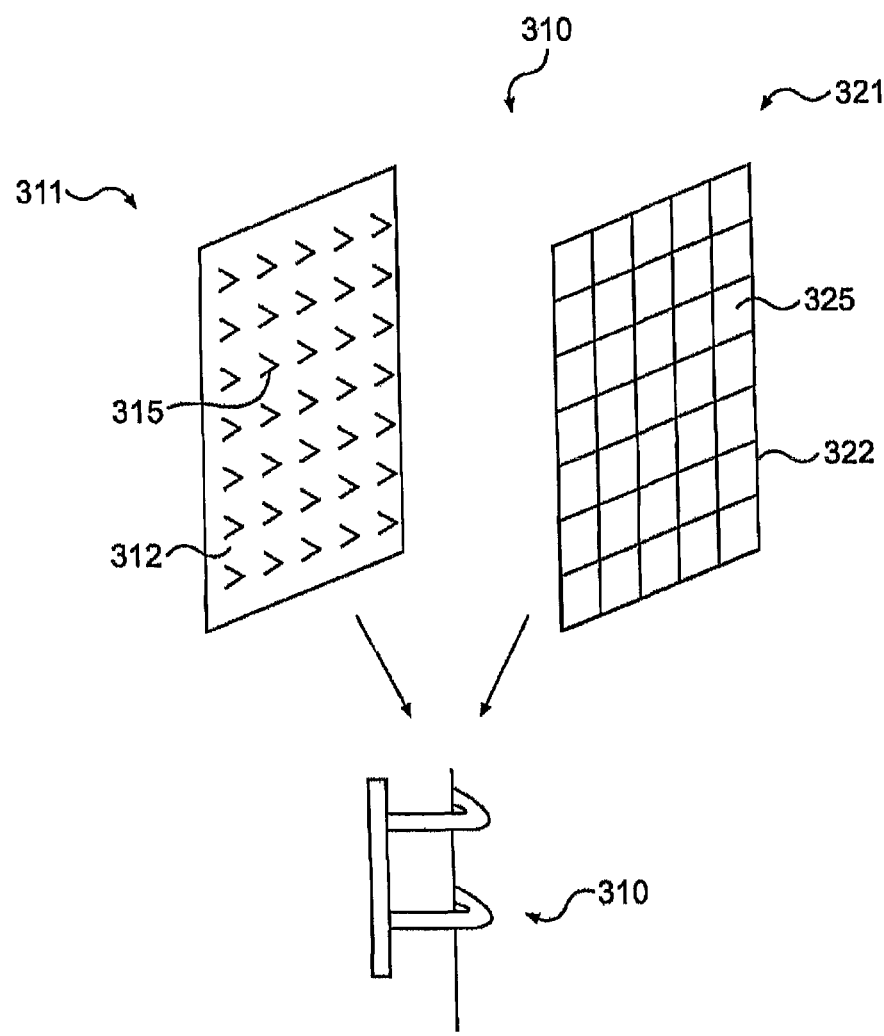
FIG. 11 is a partially expanded elevation view of another tissue fastener, according to an embodiment of the present invention.

In another embodiment of the present invention, shown in FIG. 11, a two-part fastener 310 may consist of a first part 311 and second part 321. First part 311 includes a plate 312 having a plurality of barbs 315. Barbs 315 shown in FIG. 11 are arranged in columns and rows, but other arrangements and numbers of barbs are within the scope of the invention. Second part 321 comprises a screen mesh 322 having openings 325 for receiving and retaining barbs 315. When barbs 315 pass through openings 325 in screen mesh 322, barbs 315 grip screen 322 thereby retaining first part 311 to second part 321. When first part 311 is pulled, barbs 315 grasp screen 322 preventing first part 311 from separating from second part 321. Preferably, plate 312 and mesh 322 comprise a bendable material so that connector 310 can attain a configuration like the contours of the connected tissue. In addition, fastener is preferably made of a biocompatible material, which also may be bioabsorbable. Preferred materials include nitinol, implantable grade plastic, stainless steel (316 SS), titanium, shape memory polymers such as polynorbene, polyethylene, PLLA, PGA, polyurethane, and PTFE, ceramics, and compositions of materials such as a metal and a polymer or a filled polymer. The compliance is preferably similar to that of esophageal and fundus tissue. The profile of this fastener is preferably flat. The preferred dimensions of the fastener are approximately 1-8 mm. in height and ¼-½ inches in width, and most preferably 5 mm×⅜ inches. These dimensions are not meant to limit the possible dimensions of this fastener. Additional parameters such as geometry or material compliance are not to be limited by the descriptions herein.

To use fastener 310 to fasten tissue segments, first part 311 is placed on one side of the tissue segments to be joined and second part 321 is placed on the opposite side of the tissue segments to be joined. Barbs 315 on first part 311 pierce the tissue segments to be joined and mate with screen 322 of second part 321 retaining the tissue segments therebetween.

Figure 12:
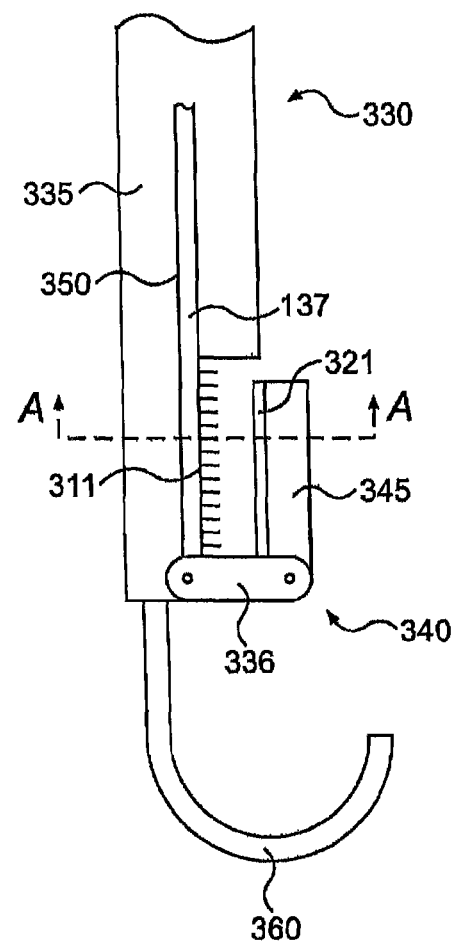
FIG. 12 is a side sectional view of a tissue fastener insertion device for use with the tissue fastener shown in FIG. 11, according to an embodiment of the present invention.
Figure 13:
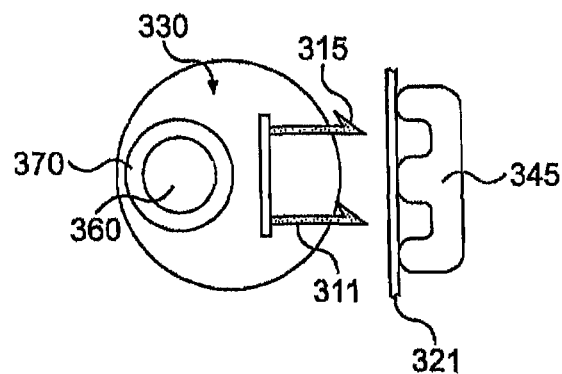
FIG. 13 is a cross-sectional view of the tissue fastener insertion device of FIG. 12, taken along line A-A.

Fastener 310 may inserted by insertion device 330, shown in FIGS. 12 and 13. Device 330 includes a main body 335 and a pivoting jaw assembly 340. Jaw assembly 340 includes a rotatable jaw 345 that mates with a distal end of body 335. Jaw 345 pivotally connects to the end of body 335 by a link 336. FIG. 12 shows jaw 345 in an essentially closed position. In that position, the second part 321 of fastener 310 is being held by jaw 345 to face the first part 311 of fastener 310 held by body 335. A pull wire 350, or other suitable actuation means, may be connected to link 336 to rotate jaw 345 to the position shown in FIG. 12. FIG. 12 also shows an endoscope 360 or other visualization device extending through a lumen 370 of body 335 (see FIG. 13) and out of a distal end of body 335. Endoscope 360 has a distal portion that may bend so that an end of the endoscope can view the operation site.

Figure 14:
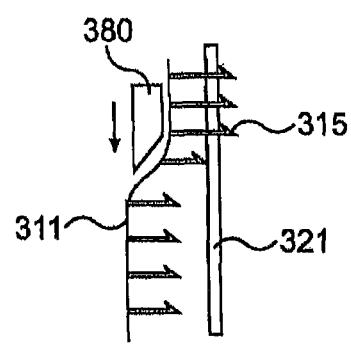
FIG. 14 is a side view of joining together of the parts of the tissue fastener of FIG. 11, according to an embodiment of the present invention.

Body 335 also may include a channel for receiving a linearly moving ramp-like structure 380 shown in FIG. 14. Ramp 380 may be moved linearly within that channel through any suitable actuation mechanism operated at the proximal end of the device outside of the patient.

In operation, the tissue segments to be secured are folded between jaw 345 and body 335 as jaw 345 is rotated to the position shown in FIG. 12 from an extended position during insertion in the esophagus. Ramp 380 then may be moved linearly within the channel in body 335 and against fastener first part 311 (as shown in FIG. 14), to urge barbs 315 through the tissue segments to be joined and into screen 322 of second part 321 and thereby retain the tissue segments between first and second parts of the fastener. It should be recognized that the invention is not limited to placing first part 311 on the body of device 330 and second part 321 on jaw 345. The positions may be reversed. It should be understood that any of the above mentioned adhesion promoting means may be combined with the fastener of FIGS. 11-14. For instance, barbs 315 may be coated with an adhesion promoting means. Additionally, an adhesion promoting means may be injected.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for fastening tissue in a patient, the method comprising:

positioning a segment of tissue between first and second members of a tissue fastening device by moving the first and second members into a closed configuration, wherein a first end of the second member is rotatably coupled to a distal end of the first member, the first member extends distally from a distal end of a tube, and in the closed configuration of the first and second members, a free end of the second member is positioned proximal to the distal end of the first member;

penetrating the segment of tissue with a tip that projects from the first member; and applying a tissue fastener to the segment of tissue, wherein at least a portion of the tissue fastener is supported from the first member during application of the tissue fastener.

2. The method of claim 1, wherein positioning the segment of tissue includes rotating the second member about the distal end of first member to hold the segment of tissue.

3. The method of claim 1, wherein penetrating the segment of tissue includes penetrating with the tip extending at one of an obtuse angle and an acute angle from an exterior surface of the first member.

4. The method of claim 3, wherein penetrating the segment of tissue includes positioning the tip in a gap between the first and second members.

5. The method of claim 1, wherein applying the tissue fastener includes penetrating the segment of tissue with the tissue fastener, and wherein the segment of tissue includes stomach tissue.

6. The method of claim 1, wherein penetrating the segment of tissue includes passing the tip completely through the segment of tissue.

7. The method of claim 1, wherein a proximal portion of the tip extends within the first member, and a distal portion of the tip projects from an exterior surface of the first member.

8. The method of claim 1, further including removing the tip from the patient after applying the tissue fastener to the segment of tissue.

9. The method of claim 1, wherein the second member includes a first leg and a second leg at an angle relative to each other.

10. A method for fastening tissue in a patient, the method comprising:

holding a segment of tissue with a device comprising first and second holding members, wherein the second holding member is rotatable relative to the first holding member, and wherein holding the segment of tissue includes folding the segment of tissue and engaging the folded segment of tissue with the first and second holding members;

penetrating the segment of tissue with first and second tips that project from at least one of the first and second holding members;

securing a tissue fastener to the segment of tissue using the device, the tissue fastener remaining external to the first and second tips during application of the tissue fastener; and removing the first and second tips from the patient after the tissue fastener is secured to the segment of tissue.

11. The method of claim 10, wherein engaging the folded segment of tissue includes rotating the second holding member relative to the first holding member about a distal end of the first holding member.

12. The method of claim 10, wherein securing the tissue fastener includes passing a portion of the tissue fastener completely through the folded segment of tissue.

13. The method of claim 10, wherein penetrating the segment of tissue includes passing at least one of the first and second tips completely through the segment of tissue.

14. The method of claim 10, wherein penetrating the segment of tissue includes positioning the first and second tips within a gap between the first and second holding members.

15. A method for fastening tissue in a patient, the method comprising:

positioning tissue between first and second segments of a tissue fastening device, wherein the second segment is rotatably coupled to the first segment, and the tissue includes stomach tissue;

penetrating at least a portion of the tissue with a tip that projects from the first segment, wherein penetrating the tissue includes positioning the tip in a gap between the first and second segments;

inserting a tissue fastener through the tissue to secure the tissue fastener to the tissue, wherein the tissue fastener includes a first end, a second end, and a connecting part extending between the first end and the second end, and radially-inward facing portions of the first end and the second end contact radially-outward facing portions of the tissue when the tissue fastener is secured; and removing the tip from the patient after the tissue fastener is secured to the tissue.

16. The method of claim 15, wherein the tip includes a needle.

17. The method of claim 16, further including delivering an adhesion promoting agent to the tissue only after the tissue fastener is secured to the tissue.

* * * * *